(12) United States Patent
Christenson et al.

(10) Patent No.: US 6,645,176 B1
(45) Date of Patent: Nov. 11, 2003

(54) SPRING LOADED IMPLANTABLE DRUG INFUSION DEVICE

(75) Inventors: Steven R. Christenson, Coon Rapids, MN (US); Reginald D. Robinson, Plymouth, MN (US); Kenneth T. Heruth, Edina, MN (US); James M. Haase, Blaine, MN (US); James Randall, Coon Rapids, MN (US); Christian Pèclat, Neuchatel (CH); Manfred K. Lüedi, Köniz (CH)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/561,583

(22) Filed: Apr. 28, 2000

(51) Int. Cl.$^7$ .................... A61M 1/00; F04B 43/08
(52) U.S. Cl. .................. 604/151; 604/153; 417/477.3; 417/477.7
(58) Field of Search .................. 604/131, 132, 604/151, 153; 417/477.1, 477.5, 477.7, 477.3, 477.8, 474, 476

(56) References Cited

U.S. PATENT DOCUMENTS

| | | | | |
|---|---|---|---|---|
| 2,804,023 A | | 8/1957 | Lee | 103/149 |
| 2,920,578 A | | 1/1960 | Schaurte | 103/149 |
| 3,644,068 A | * | 2/1972 | Lepak | 417/477 |
| 3,822,948 A | * | 7/1974 | Handl | 401/146 |
| 3,885,894 A | | 5/1975 | Sikes | 417/477 |
| 3,918,453 A | | 11/1975 | Leonard | 128/278 |
| 3,927,955 A | * | 12/1975 | Spinosa et al. | 417/477 |
| 3,960,466 A | | 6/1976 | Taylor | 417/234 |
| 3,963,023 A | * | 6/1976 | Hankinson | 128/214 F |
| 3,990,444 A | | 11/1976 | Vial | 128/214 F |
| 4,012,177 A | | 3/1977 | Yakich | 417/477 |
| 4,013,074 A | | 3/1977 | Siposs et al. | 128/260 |
| 4,256,437 A | | 3/1981 | Brown | 417/45 |
| 4,525,164 A | * | 6/1985 | Loeb et al. | 604/131 |
| 4,545,744 A | | 10/1985 | Weber et al. | 417/475 |
| 4,564,342 A | | 1/1986 | Weber et al. | 417/477 |
| 4,576,556 A | | 3/1986 | Thompson | 417/477 |
| 4,650,471 A | | 3/1987 | Tamari | 604/153 |
| 4,685,902 A | | 8/1987 | Edwards et al. | 604/153 |
| 4,692,147 A | | 9/1987 | Duggan | |

(List continued on next page.)

FOREIGN PATENT DOCUMENTS

| | | |
|---|---|---|
| DE | 24 52 771 | 11/1974 |
| DE | 3737023 | 7/1988 |
| DE | 101 19391 | 4/2001 |
| EP | 0 174 535 | 8/1985 |
| EP | 0 239 255 | 2/1987 |
| EP | 0320441 | 10/1988 |
| EP | 0 547 550 B1 | 3/1998 |
| FR | 2 021 524 | 7/1970 |
| FR | 2 644 853 | 3/1989 |
| FR | 2 719 873 | 5/1994 |
| FR | 2 808 203 | 3/2001 |
| GB | 681 | of 1902 |
| SU | 547550 | 2/1977 |

OTHER PUBLICATIONS

"STA–PURE peristaltic pump tube," Watson–Marlow Bredel product brochure.
"OEM: Peristaltic Pumps for Engineers," Watson–Marlow Limited product brochure.
"OEM: Custom Pump Catalog," Watson–Marlow Bredel product catalog.

(List continued on next page.)

Primary Examiner—Michael J. Hayes

(57) ABSTRACT

An implantable drug infusion device includes a pump tube for holding a liquid to be pumped. A race is configured to support the tube. A roller assembly is configured to compress the tube against the race at one or more points along the path, and the roller assembly includes at least one roller. A drive assembly drives the roller assembly relative to the tube along the path so as to move the liquid through the tube. A biasing member is operably connected to the at least one roller to bias the at least one roller against the tube.

24 Claims, 10 Drawing Sheets

U.S. PATENT DOCUMENTS

| | | | |
|---|---|---|---|
| 4,950,136 A | 8/1990 | Haas et al. | 417/477 |
| 5,064,358 A | 11/1991 | Calarai | 417/475 |
| 5,082,429 A | 1/1992 | Soderquist et al. | 417/477 |
| 5,083,908 A | 1/1992 | Gagnebin et al. | 417/477 |
| 5,096,393 A | 3/1992 | Van Steenderen et al. | 417/477 |
| 5,125,801 A | 6/1992 | Nabity et al. | 417/44 |
| 5,213,483 A | 5/1993 | Flaherty et al. | 417/477 |
| 5,215,450 A | 6/1993 | Tamari | 417/474 |
| 5,266,013 A | 11/1993 | Aubert et al. | 417/474 |
| 5,576,503 A | 11/1996 | Nabity et al. | 73/863.01 |
| 5,578,001 A | 11/1996 | Shah | 604/31 |
| 5,741,125 A | 4/1998 | Neftel et al. | 417/477.7 |
| 5,840,069 A | 11/1998 | Robinson | 604/131 |
| 5,915,932 A | 6/1999 | Nabity et al. | 417/477.1 |
| 6,036,459 A | 3/2000 | Robinson | 417/477.7 |

OTHER PUBLICATIONS

U.S. patent application Ser. No. 09/834,874, entitled "Implantable Drug Delivery Device with Peristaltic Pump Having a Retracting Roller", filed Apr. 13, 2001. (P–9175.00).

U.S. patent application Ser. No. 09/835,208, entitled "Implantable Drug Delivery Device with Peristaltic Pump Having a Bobbin Roller Assembly", filed Apr. 13, 2001. (P–9274.00).

U.S. patent application Ser. No. 09/561,154, entitled "Implantable Drug Infusion Device with Peristaltic Pump Using Tube Guide", filed Apr. 28, 2000. (P–9176.00).

* cited by examiner

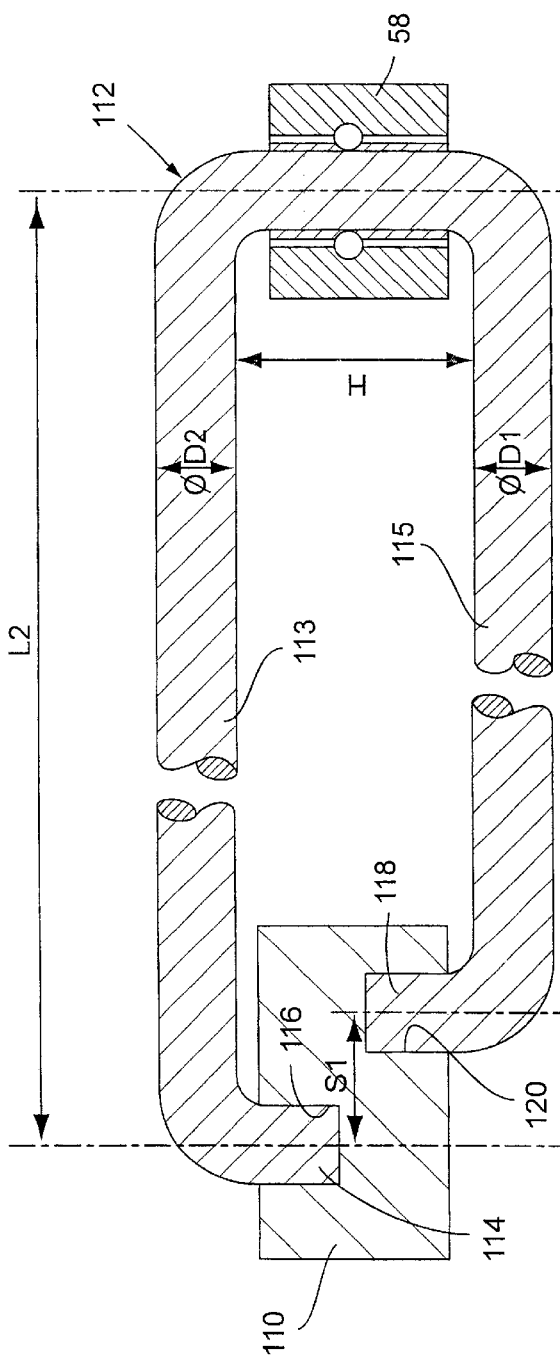
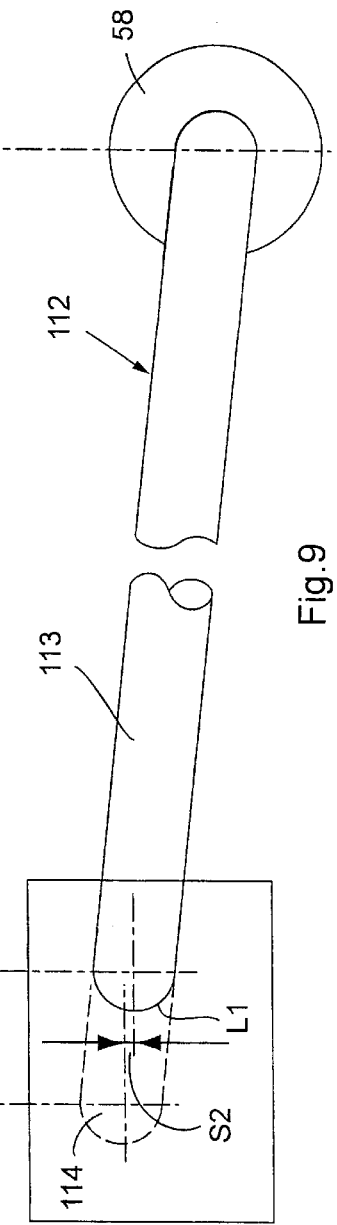
Fig. 8
Fig. 9

SPRING LOADED IMPLANTABLE DRUG INFUSION DEVICE

RELATED APPLICATIONS

The following applications are related to the present application: "Implantable Drug Delivery Device with Peristaltic Pump Having a Bobbin Roller Arm", assigned Ser. No. 09/835,208, filed on Apr. 13, 2001; and "Implantable Drug Delivery Device with Peristaltic Pump Having Retractable Rollers, assigned Ser. No. 09/834,874, filed on Apr. 13, 2001.

BACKGROUND OF THE INVENTION

1. Field of the Invention

The present invention relates to an implantable drug delivery device for infusing a therapeutic agent into an organism, and more particularly, relates to an improved peristaltic implantable pump with improved occlusion along a fluid tube.

2. Description of the Related Art

Implantable drug infusion devices are well known in the art. These devices typically include a medication reservoir within a generally cylindrical housing. Some form of fluid flow control is also provided to control or regulate the flow of fluid medication from the reservoir to the outlet of the device for delivery of the medication to the desired location in a body, usually through a catheter. These devices are used to provide patients with a prolonged dosage or infusion of a drug or other therapeutic agent.

Active drug infusion devices feature a pump or a metering system to deliver the drug into the patient's system. An example of such a drug infusion pump currently available is the Medtronic SynchroMed programmable pump. Additionally, U.S. Pat. No. 4,692,147 (Duggan), U.S. Pat. No. 5,840,069 (Robinson), and U.S. Pat. No. 6,036,459 (Robinson), assigned to Medtronic, Inc., Minneapolis, Minn., disclose body-implantable electronic drug administration devices comprising a peristaltic (roller) pump for metering a measured amount of drug in response to an electronic pulse generated by control circuitry associated within the device. Each of these patents is incorporated herein by reference in their entirety for all purposes. Such pumps typically include a drug reservoir, a fill port, a peristaltic pump having a motor and a pumphead to pump out the drug from the reservoir, and a catheter port to transport the drug from the reservoir via the pump to a patient's anatomy. The drug reservoir, fill port, peristaltic pump, and catheter port are generally held in a housing, or bulkhead. The bulkhead typically has a series of passages extending from the drug reservoir and through the peristaltic pump that lead to the catheter port, which is typically located on the side of the housing. The peristaltic pumps use rollers which move along a pump tube, thereby moving liquid through the tube.

The prior art delivery devices, however, are limiting in that the load that the rollers place on the tube can vary as the rollers move along the tube. If the load is excessive, excess energy will be consumed and the tube life will be shortened, resulting in increased replacement costs. If the load is insufficient, inadequate occlusion of the tube will result in leakage of fluid past the roller, reducing the accuracy of the pump. Variation in the load is caused by variations in the gap between the rollers and the race in which the pump tube lies, the gap variance being due to manufacturing tolerances associated with the tube, the race and the pumphead. Prior art solutions to the load variance problem include tight manufacturing tolerances, sorting and matching of components, and placing shims of appropriate thickness between the rollers and the tube, each of which increases manufacturing costs and reduces manufacturing flexibility.

It is an object of the present invention to provide an implantable drug infusion device which reduces or wholly overcomes some or all of the difficulties inherent in prior known devices. Particular objects and advantages of the invention will be apparent to those skilled in the art, that is, those who are knowledgeable or experienced in this field of technology, in view of the following disclosure of the invention and detailed description of preferred embodiments.

SUMMARY OF THE INVENTION

The present invention provides an implantable drug infusion device which features a peristaltic pump having a new configuration, in which a spring biases a roller assembly against a pump tube, thereby minimizing the variation in the load that the roller assembly places on the pump tube.

In accordance with a first aspect, an implantable drug infusion device includes an implantable drug infusion device including a pump tube for holding a liquid to be pumped. A race is configured to support the tube along a path. A roller assembly is configured to compress the tube against the race at one or more points along the path, and the roller assembly includes at least one roller. A drive assembly drives the roller assembly relative to the tube along the path so as to move the liquid through the tube. A biasing member is operably connected to the at least one roller to adjustably bias the at least one roller against the tube.

In accordance with another aspect, an implantable drug infusion device includes a bulkhead having a race. A pump tube having an inlet and an outlet is positioned within the race. A roller assembly is configured to compress the tube against the race at at least one point along the path, and the roller assembly includes at least one roller. A drive assembly drives the roller assembly relative to the tube along the path so as to move a liquid through the tube. A biasing member is operably connected to the at least one roller to adjustably bias the at least one roller against the tube.

In accordance with yet another aspect, an implantable drug infusion device includes a bulkhead having a race, a first chamber, and a second chamber. A pump tube has an inlet and an outlet and is positioned within the race. A motor assembly is positioned within the first chamber, a pumphead assembly is positioned within the second chamber, and the motor assembly drives the pumphead assembly. The pumphead assembly includes a roller assembly having a hub and three trailing arms. Each trailing arm has a roller and is pivotally connected to the hub. A drive assembly drives the roller assembly relative to the tube along the path so the rollers compress the tube to move a liquid through the tube. A spring is operably connected to each trailing arm to bias a corresponding roller against the tube.

From the foregoing disclosure, it will be readily apparent to those skilled in the art, that is, those who are knowledgeable or experienced in this area of technology, that the present invention provides a significant advance over the prior art. Preferred embodiments of the implantable infusion device of the present invention can significantly reduce the variation in load placed by the roller assembly on the pump tube. This will allow for less stringent manufacturing tolerances, increased manufacturing flexibility, increased tube life, and improved performance. These and additional features and advantages of the invention disclosed here will be further understood from the following detailed disclosure of preferred embodiments.

BRIEF DESCRIPTION OF THE DRAWINGS

Preferred embodiments are described in detail below with reference to the appended drawings. The accompanying drawings, which are incorporated into and form a part of this specification, together with the description, serve to explain the principles of the invention. The drawings are not drawn necessarily to scale, are only for the purpose of illustrating a preferred embodiment of the invention, and are not to be construed as limiting the invention. Some features of the implantable drug infusion device depicted in the drawings have been enlarged or distorted relative to others to facilitate explanation and understanding. The above mentioned and other advantages and features of the invention will become apparent upon reading the following detailed description and referring to the accompanying drawings in which like numbers refer to like parts throughout and in which:

FIG. 8 is a section view of an alternative embodiment of the roller arm assembly of FIG. 1;

FIG. 9 is a plan view of the roller arm assembly of FIG. 8;

DESCRIPTION OF THE PREFERRED EMBODIMENTS

Figure 1:
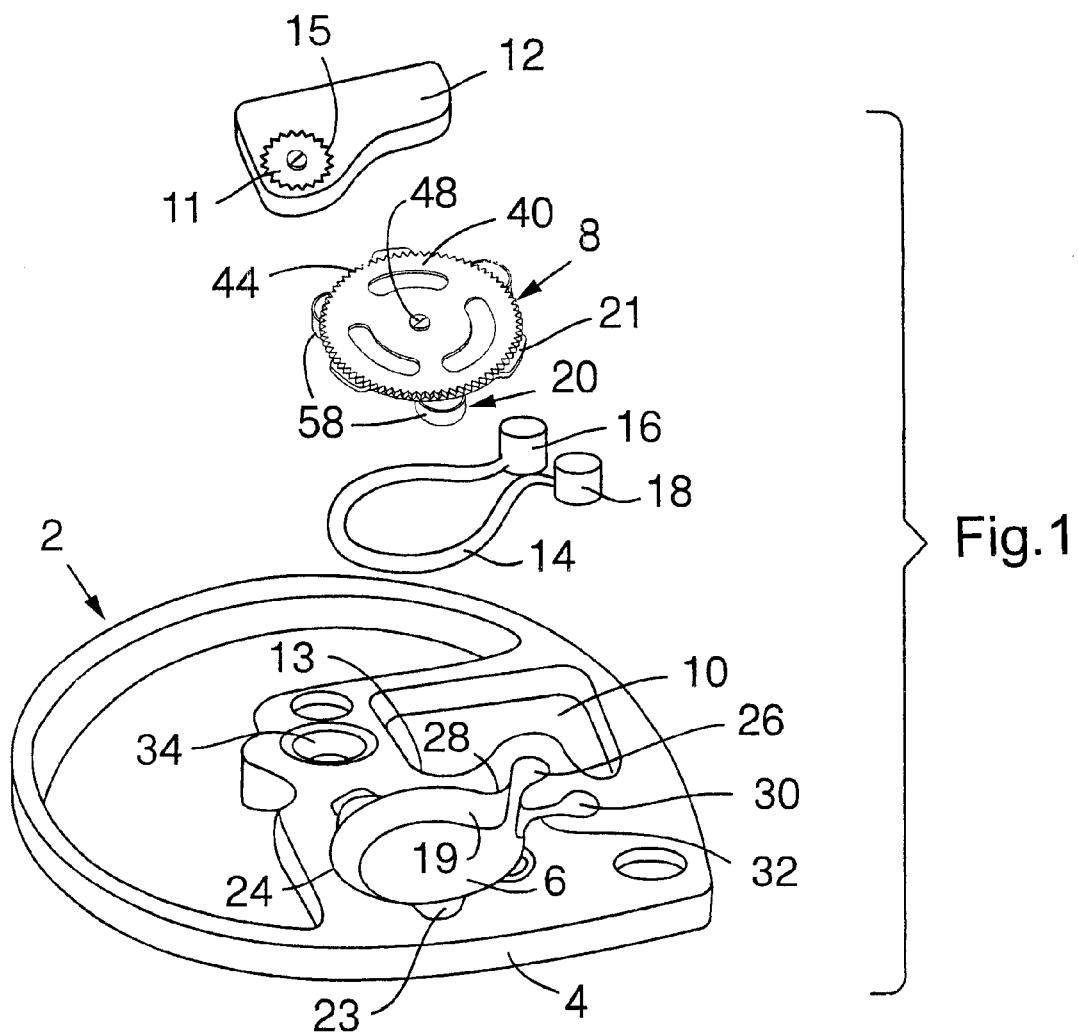
FIG. 1 is an exploded perspective view of an implantable drug infusion device in accordance with the present invention.

As shown in FIG. 1, an implantable drug infusion device 2 in accordance with the invention comprises a bulkhead 4 containing a number of chambers and cavities sized and configured to house various subsystems of the implantable drug infusion device. In particular, bulkhead 4 has a first chamber 6 sized and configured to house a peristaltic pumphead assembly 8. A second chamber 10, sized and configured to house a motor assembly 12 which drives pumphead assembly 8, is positioned adjacent first chamber 6 and separated therefrom by a wall 13. Other chambers of bulkhead 4 house a battery and the electronic circuitry (not shown) used to operate implantable drug infusion device 2 and to control the dosage rate of the medication into the body.

Pumphead assembly 8 includes a compression member, such as roller arm assembly 20, for compressing a pump tube 14 having an inlet 16 and an outlet 18. First chamber 6 has a generally circular wall 24 defining a pump race 19. Pump tube 14 is placed in first chamber 6 in close proximity to wall 24 so that roller arm assembly 20 may force the tube against the wall, thereby forcing medication to move through the tube in a known peristaltic manner. Flanges 21 extending outwardly from pumphead assembly 8 are received in recesses 23 formed in first chamber 6, supporting pumphead assembly 8 in first chamber 6. Inlet 16 is placed in a pump inlet cavity 26 formed in bulkhead 4. Pump inlet cavity 26 is connected to the pump race 19 by a pump inlet race ramp 28. Pump tube outlet 18 is placed in a pump outlet cavity 30 formed in bulkhead 4. Pump tube outlet cavity 30 is connected to the pump race 19 by a pump outlet race ramp 32. In a preferred embodiment, both pump inlet race ramp 28 and pump outlet race ramp 32 have an arcuate geometry to reduce pumphead torque, as described in greater detail below. A cover (not shown) is also provided for bulkhead 4 to provide protection for the components of drug infusion device 2. Motor assembly 12 includes a motor (not shown) which drives a four-stage gear assembly 11, only the fourth stage of which is visible. Teeth 15 are formed on the periphery of the fourth stage of gear assembly 11.

Bulkhead 4 has an integral fill port cavity 34, sized and configured to house a septum and components to retain the septum. Drugs are injected through the septum to fill a reservoir (not shown) contained within a lower portion of bulkhead 4. A pathway is formed between the reservoir and pump inlet cavity 28, through which drugs are introduced into pump tube 14. The drugs exit pump outlet cavity 30 and travel through another pathway formed in bulkhead 4 to a catheter port on the periphery of bulkhead 4 from which the drug exits the device 2 and enters the anatomy of the individual. The structure of the septum, retaining components, pathways, and catheter port are known to one of skill in the art and are not shown here.

Figure 2:
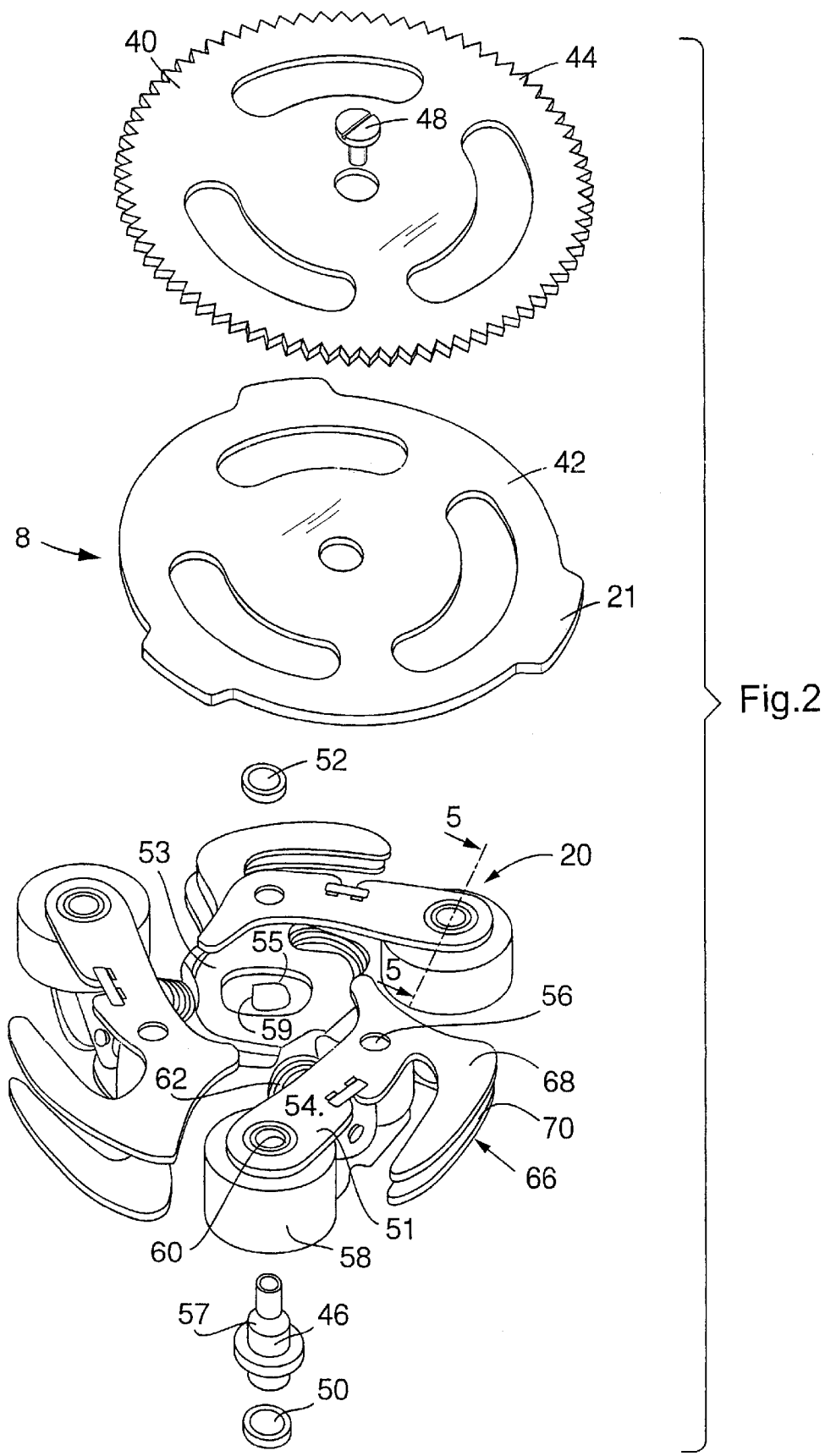
FIG. 2 is an exploded perspective view of a pumphead assembly of the implantable device of FIG. 1.

Referring now to FIG. 2, pumphead assembly 8 is shown in exploded form. Pumphead assembly 8 includes a drive gear 40 with teeth 44 formed about its periphery. A support plate 42 is positioned below drive gear 40. Flanges 21 extend outwardly from support plate 42 and, as described above, are received in recesses 23 of bulkhead 4, and preferably welded thereto. Roller arm assembly 20 is positioned below support plate 42. Drive shaft 46 extends axially through apertures in roller arm assembly 20, support plate 42, and drive gear 40, and is retained by retaining screw 48. Drive shaft 46 is supported for rotation at its lower end by lower bearing 50, and at a central location, between roller arm assembly 20 and support plate 42, by upper bearing 52.

Figure 5:
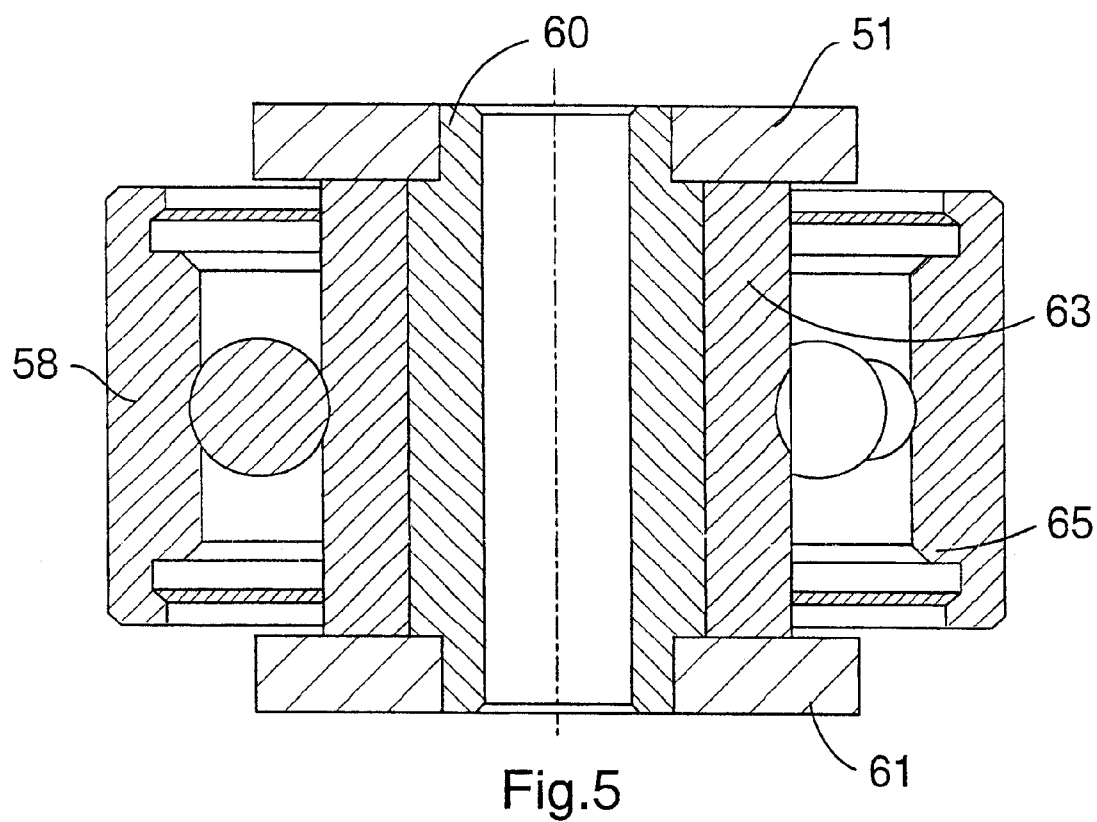
FIG. 5 is a section view, taken along lines 5—5 of FIG. 2, of a trailing arm of the implantable device of FIG. 1.

Roller arm assembly 20 comprises a central hub 53 having an aperture 55 through which drive shaft 46 extends. Flat 57 on drive shaft 46 mates with flat 59 of aperture 55 such that roller arm assembly 20 rotates as drive shaft 46 rotates. A plurality of trailing arms 54 are each pivotally secured by a pin 56 to hub 53. Trailing arm 54 comprises upper plate 51 and lower plate 61. A roller 58 is pivotally secured to each trailing arm 54 by an axle 60. As seen in FIG. 5, axle 60 extends between upper and lower plates 51, 61. Axle 60 passes through an inner race 63 of roller 58. Inner race 63 is extended vertically to provide clearance between an outer race 65 of roller 58 and upper and lower plates 51, 61. In the illustrated embodiment, roller arm assembly 20 is shown with three trailing arms 54 and three corresponding rollers 58, however, the number of trailing arms 54 and rollers 58 may be greater or lesser than three.

Figure 3:
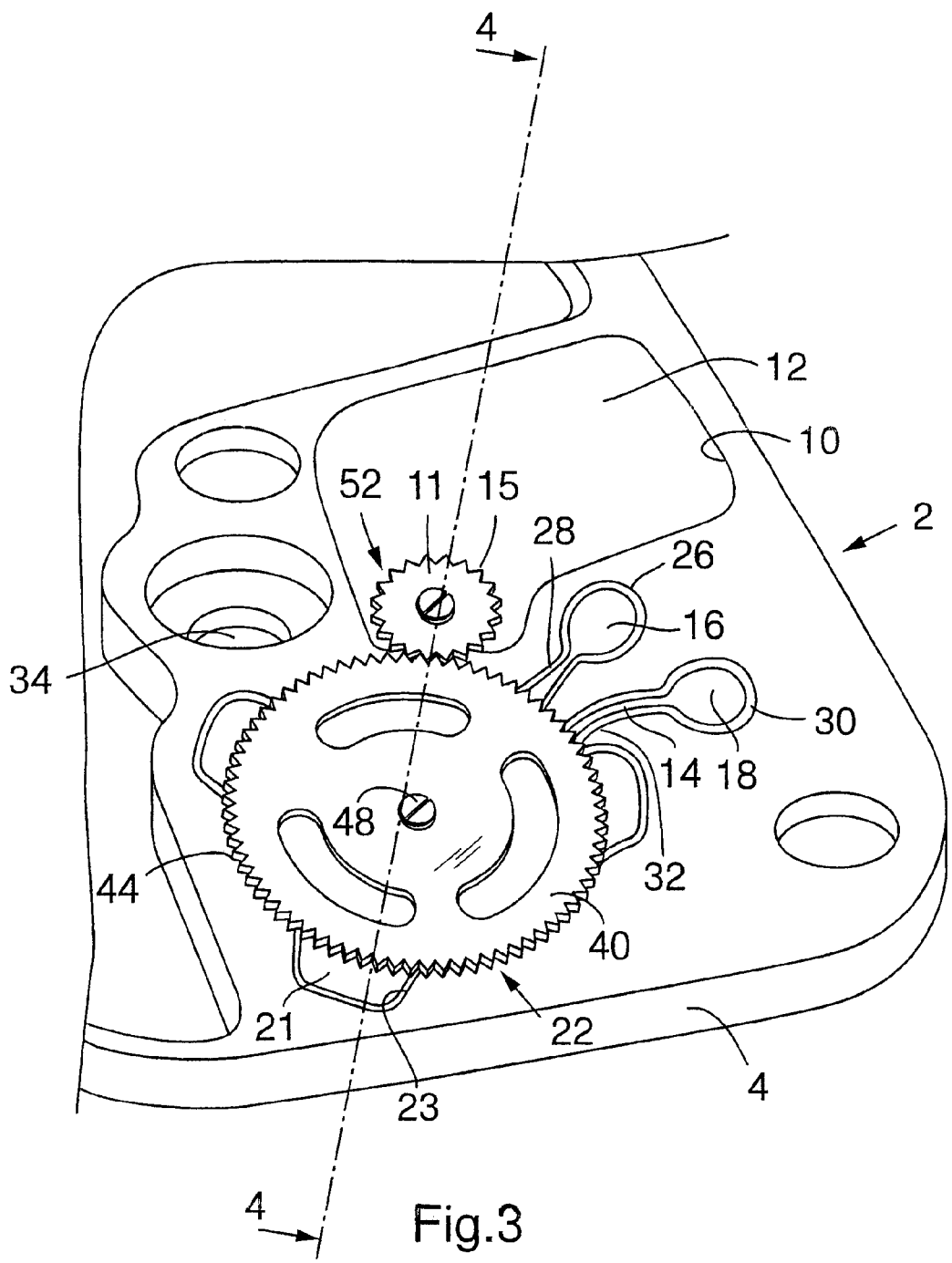
FIG. 3 is perspective view, partially cut away, of the implantable device of FIG. 1, shown in its assembled state.
Figure 4:
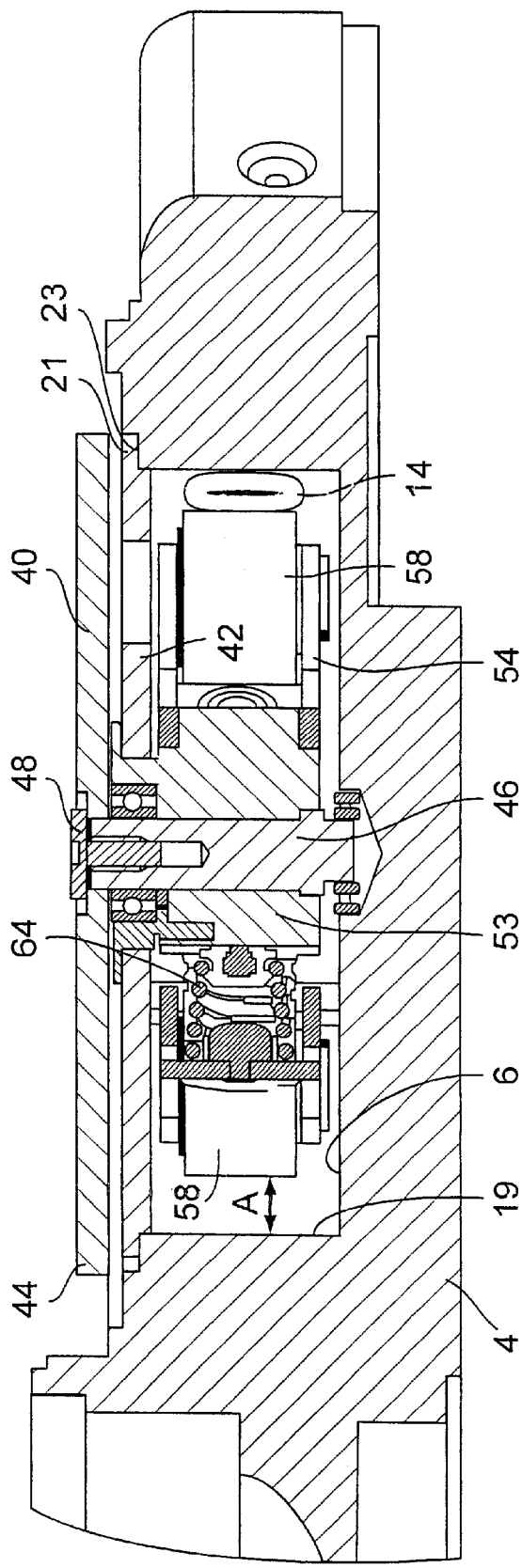
FIG. 4 is a section view, taken along lines 4—4 of FIG. 3, of the implantable device of FIG. 1.

As seen in FIGS. 3 and 4, teeth 15 of gear assembly 11 drivingly engage teeth 44 of drive gear 42, thereby causing rollers 58 to move about race 19, compressing and occluding tube 14 as they move and forcing the drug therethrough in known peristaltic fashion. As noted above, inlet race ramp 28 and outlet race ramp 32 each have an arcuate geometry, which reduces the torque required as each roller 58 engages pump tube 14 during rotation of roller arm assembly 20.

Referring back to FIG. 2, each trailing arm 54 and its corresponding roller 58 is adjustably biased outwardly by a biasing member, such as spring 62. In a preferred embodiment, spring 62 is a coil spring. As seen in FIG. 4, spring 62 is oriented to facilitate the occlusion, or compression, of tube 14 by roller 58. Since manufacturing tolerances on the system components, i.e., roller 58, tube 14 and race 19, can result in variations in the gap A between roller 58 and race 19, the biasing action of spring 62 can advantageously minimize the variation in load placed by roller 58 on tube 14, greatly increasing the compliance of the system. Thus, for an incremental change in the gap between roller 58 and race 19, the incremental load required is reduced. For example, in prior art devices, where the system compliance is accounted for by the tube itself, a 0.001" decrease in a radial direction of the race could incur a 150 g load increase on roller 58. With the present invention, however, spring 62 may be sized with a spring rate such that for a 0.001" decrease in the race, a 1.5 g increase in load is realized. In a preferred embodiment, spring 62 is formed of a highly corrosion resistant and fatigue resistant alloy. Suitable materials include cobalt alloys and stainless steel. In other preferred embodiments, a nitinol shape memory alloy may be used for spring 62.

The biasing member provides numerous advantages over the prior art devices. Reducing the variation in load prevents excessive loading, thereby providing increased tube life; minimizes the force needed to occlude the pump tube, thereby minimizing the torque requirement for occlusion; improves occlusion and, therefore, reducing leakage and improving the performance of the peristaltic pump; allows for looser manufacturing tolerances and minimizes the need for sorting and matching components, providing increased manufacturing flexibility and reducing costs.

In a preferred embodiment, as seen in FIG. 2, roller arm assembly 20 further includes a tube guide 66. In the illustrated embodiment, tube guide 66 is connected to trailing arm 54 and is formed of an upper plate 68 and a lower plate 70. In another preferred embodiment, tube guide 66 may be connected directly to hub 53. Tube guide 66 serves to help keep pump tube 14 properly aligned to ensure that rollers 58 are centered with respect to pump tube 14.

Figure 6:
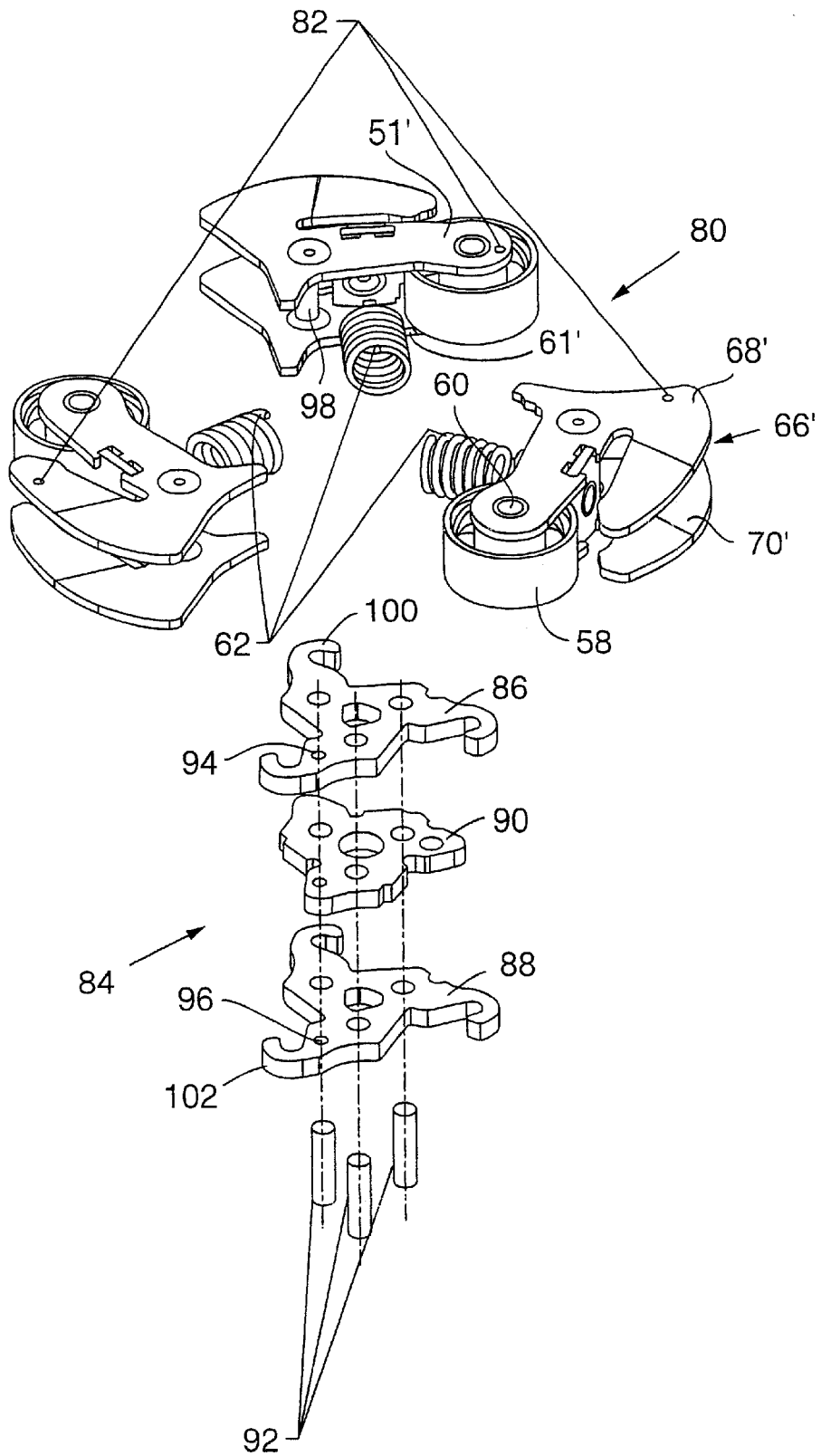
FIG. 6 is an exploded perspective view of an alternative embodiment of the roller arm assembly of FIG. 1.

Another embodiment of a roller arm assembly 80 is shown in FIG. 6. Roller arm assembly 80 comprises three trailing arms 82 pivotally secured to a hub 84. Hub 84 comprises upper plate 86, lower plate 88, and center plate 90. Rods 92 extend through apertures 94, 96 formed in upper plate 86 and lower plate 88, respectively. Pivot pins 98 extend between upper plate 51' and lower plate 61' of each trailing arm 82. Hooks 100, 102 formed on upper plate 86 and lower plate 88, respectively, of hub 84, capture pivot pins 98. The force of springs 62 acting on trailing arms 82 helps maintain trailing arms 82 in position on hub 84.

It is to be appreciated that other roller arm assembly constructions will be suitable, and are considered within the scope of the present invention. Suitable roller arm assembly constructions will provide a biasing member to ensure that a roller, or other suitable compression member, is biased against a pump tube, thereby minimizing the variation in load required to occlude the pump tube. Other suitable biasing members include, for example, leaf springs and springs of other constructions, elastomeric members, closed or open cell elastomeric foam members, torsion bars, magnetic members, and solenoids.

Figure 7:
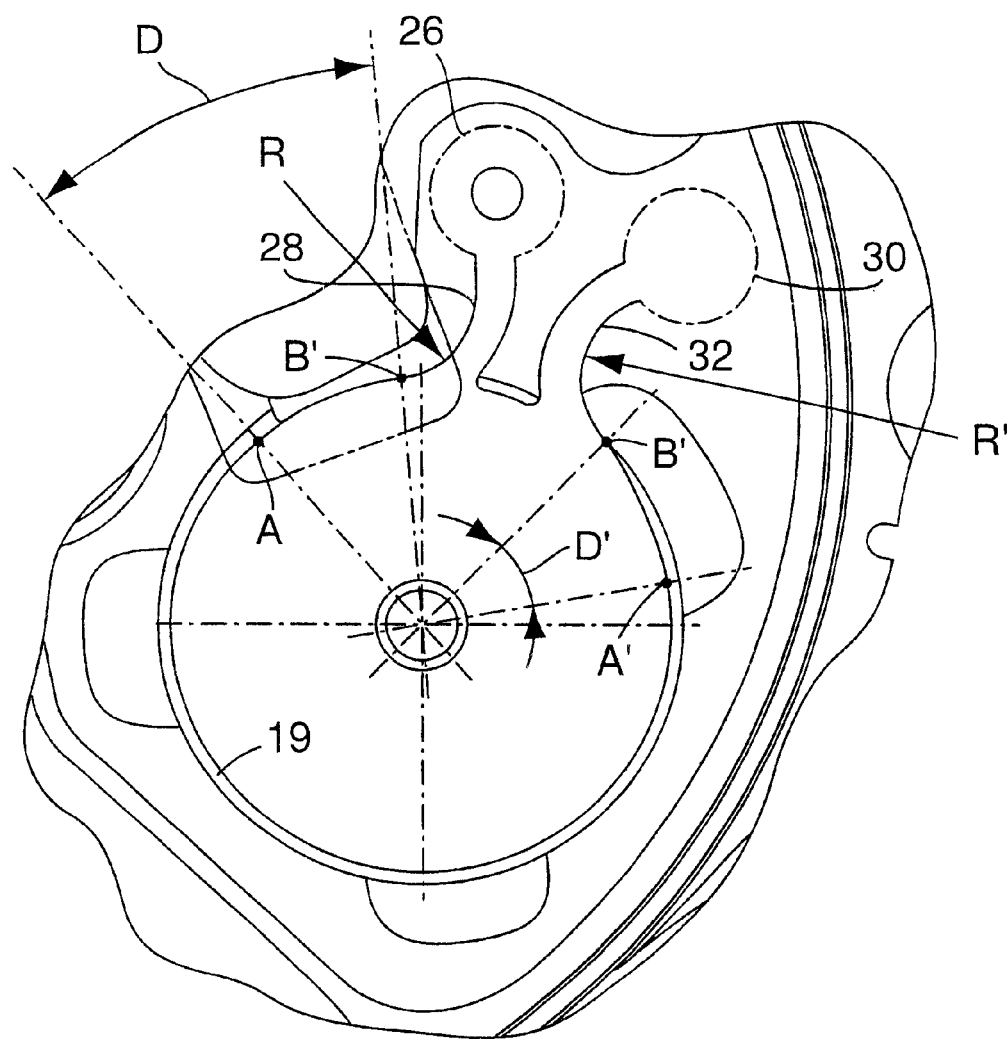
FIG. 7 is a plan view of the geometry of the race and inlet and outlet ramps of the implantable device of FIG. 1.

In a preferred embodiment, inlet and outlet ramps 28 and 32 have exit and entry ramps transitioning smoothly into and from race 19 in order to minimize drag torque on pumphead assembly 8. As seen in FIG. 7, inlet ramp 28 transitions smoothly from a radius R of approximately 3.947 mm (0.1554 in) through point B to point A of race 19. Race 19 then transitions from point A' to point B and then through a radius R' of approximately 4.02 mm (0.1583 mm). The angles D, D' between points A and B, and A' and B', respectively are approximately 35.5°. Shown in the table below are the dimensions for the radius of race 19 along the arc between points A and B, and A' and B', in 0.5° increments. It is to be appreciated that the radius varies smoothly along race 19.

| Angle | Radius |
|---|---|
| 0.0° | 11.0000 |
| .5 | 11.0054 |
| 1.0 | 11.0108 |
| 1.5 | 11.0162 |
| 2.0 | 11.0216 |
| 2.5 | 11.0270 |
| 3.0 | 11.0324 |
| 3.5 | 11.0378 |
| 4.0 | 11.0432 |
| 4.5 | 11.0486 |
| 5.0 | 11.0540 |
| 5.5 | 11.0594 |
| 6.0 | 11.0648 |
| 6.5 | 11.0702 |
| 7.0 | 11.0756 |
| 7.5 | 11.0810 |
| 8.0 | 11.0864 |
| 8.5 | 11.0918 |
| 9.0 | 11.0972 |
| 9.5 | 11.1026 |
| 10.0 | 11.1080 |
| 10.5 | 11.1134 |
| 11.0 | 11.1188 |
| 11.5 | 11.1242 |
| 12.0 | 11.1296 |
| 12.5 | 11.1350 |
| 13.0 | 11.1404 |
| 13.5 | 11.1458 |
| 14.0 | 11.1512 |
| 14.5 | 11.1566 |
| 15.0 | 11.1620 |
| 15.5 | 11.1674 |
| 16.0 | 11.1728 |
| 16.5 | 11.1782 |
| 17.0 | 11.1836 |
| 17.5 | 11.1890 |
| 18.0 | 11.1944 |
| 18.5 | 11.1998 |
| 19.0 | 11.2052 |
| 19.5 | 11.2106 |
| 20.0 | 11.2160 |
| 20.5 | 11.2214 |
| 21.0 | 11.2268 |
| 21.5 | 11.2322 |
| 22.0 | 11.2376 |
| 22.5 | 11.2430 |
| 23.0 | 11.2484 |
| 23.5 | 11.2538 |
| 24.0 | 11.2592 |
| 24.5 | 11.2646 |
| 25.0 | 11.2700 |
| 25.5 | 11.2754 |
| 26.0 | 11.2808 |
| 26.5 | 11.2862 |
| 27.0 | 11.2916 |

-continued

| Angle | Radius |
|-------|--------|
| 27.5 | 11.2970 |
| 28.0 | 11.3024 |
| 28.5 | 11.3078 |
| 29.0 | 11.3132 |
| 29.5 | 11.3186 |
| 30.0 | 11.3240 |
| 30.5 | 11.3294 |
| 31.0 | 11.3348 |
| 31.5 | 11.3402 |
| 32.0 | 11.3456 |
| 32.5 | 11.3510 |
| 33.0 | 11.3564 |
| 33.5 | 11.3618 |
| 34.0 | 11.3672 |
| 34.5 | 11.3726 |
| 35.0 | 11.3780 |
| 35.5 | 11.3834 |

Another preferred embodiment is shown in FIGS. 8 and 9, in which the biasing member is formed as an arm 112. Arm 112 is formed of a length of wire bent into a desired shape. Roller 58 is secured to a hub 110 via an arm 112. Arm 112 has a substantially U shaped profile forming upper and lower arms 113, 115 and extends through roller 58. An end 114 of upper arm 113 is bent and received in an aperture 116 in an upper surface of hub 110, and an end 118 of lower arm 115 is bent and received in an aperture 120 in a lower surface of hub 110. The upper and lower arms 113, 115 are of unequal length L1 and L2, respectively, such that apertures 116 and 120 are offset from one another in a radial direction with respect to hub 110 by a distance S1. Ends 114 and 118 may also be offset from one another in an axial direction with respect to hub 110 by a distance S2. In an equilibrium state, there is no stress on arm 112, and, therefore, no stress placed on roller 58.

Figure 10:
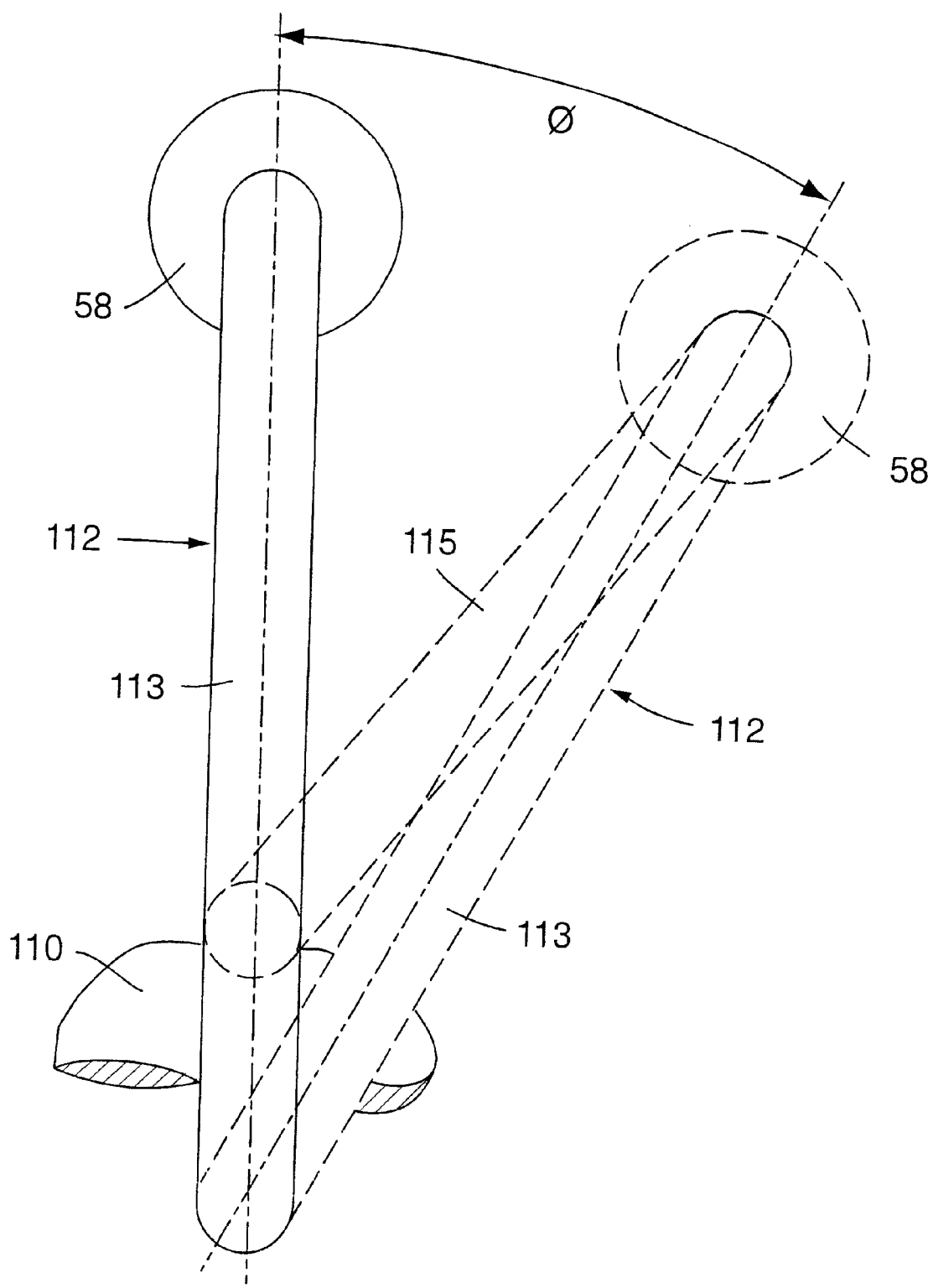
FIG. 10 is a plan view of the roller arm assembly of FIG. 8, showing the roller arm assembly before and after being compressed.

As seen in FIG. 10, as arm 112 is rotated an angular amount θ with respect to hub 110 (to the position shown in dashed lines), the upper and lower arms 113, 115 become misaligned, placing stress on arm 112 and exerting a torque, and, therefore, a biasing effect on rollers 58. The amount of torque can be varied by selecting appropriate lengths and diameters for upper and lower arms 113, 115, varying the height of arm 112, and varying the offsets S1 and S2 between upper and lower arms 113, 115.

Figure 11:
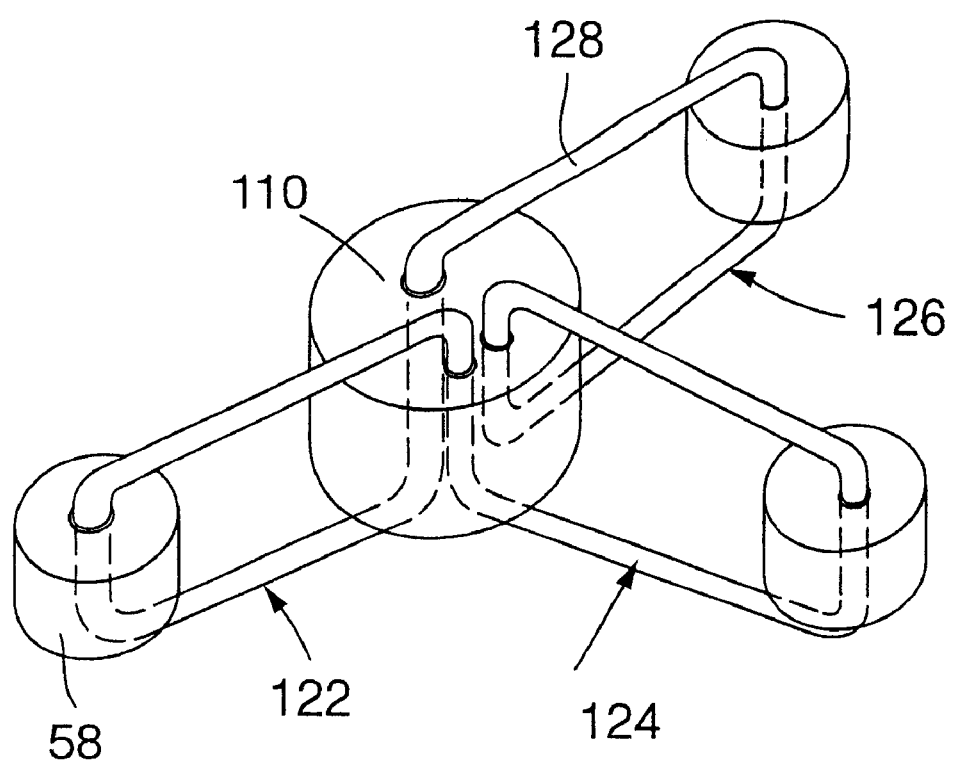
FIG. 11 is a perspective view of an alternative embodiment of the roller arm assembly of FIG. 8.

Another embodiment is shown in FIG. 11, wherein three arms 122, 124, 126, each having a configuration similar to that described above with respect to FIGS. 8, 9, are formed from a single wire 128. As illustrated, wire 128 extends through a hub 110, however, it is to be appreciated that hub 110 is not required, and the arms 122, 134, 126 may act as biasing members without the use of a hub.

In light of the foregoing disclosure of the invention and description of the preferred embodiments, those skilled in this area of technology will readily understand that various modifications and adaptations can be made without departing from the scope and spirit of the invention. All such modifications and adaptations are intended to be covered by the following claims.

What is claimed is:

1. An implantable drug infusion device comprising, in combination:
   a pump tube for holding a liquid to be pumped;
   a race configured to support the tube along a path;
   a roller assembly configured to compress the tube against the race at one or more points along the path, the roller assembly including at least one roller; and
   a drive assembly to drive the roller assembly relative to the tube along the path so as to move the liquid through the tube;
   wherein the roller assembly comprises at least one trailing arm pivotally connected to the roller assembly, each trailing arm having a roller pivotally secured at one end of the trailing arm, a biasing member to adjustably bias the roller against the pump tube, and a tube guide extending from the other end of the trailing arm to align the pump tube with respect to a corresponding roller.

2. The implantable drug infusion device of claim 1, wherein the biasing member comprises a coil spring.

3. The implantable drug infusion device of claim 1, wherein the race includes an inlet ramp and an outlet ramp.

4. The implantable drug infusion device of claim 3, wherein the inlet ramp has an arcuate geometry.

5. The implantable drug infusion device of claim 3, wherein the outlet ramp has an arcuate geometry.

6. The implantable drug infusion device of claim 1, wherein the roller assembly comprises three trailing arms.

7. The implantable drug infusion device of claim 1, wherein each biasing member comprises a coil spring.

8. The implantable drug infusion device of claim 1, wherein the drive assembly comprises a drive shaft and a drive gear, the drive gear configured to be rotatably driven by a motor, the drive shaft rotatably driven by the drive gear and rotatably driving the roller assembly.

9. The implantable drug infusion device of claim 8, wherein the drive gear includes a plurality of teeth about a periphery of the drive gear engageable by a gear of a motor assembly.

10. The implantable drug device of claim 1, wherein the biasing member comprises an arm formed of a length of wire.

11. The implantable drug device of claim 1, wherein the biasing member comprises arm formed of a length of wire and operably connected to three rollers.

12. The implantable drug infusion device of claim 1, wherein each tube guide comprises an upper blade and a lower blade.

13. An implantable drug infusion device comprising, in combination:
    a pump tube for holding a liquid to be pumped;
    a race configured to support the tube along a path;
    a roller assembly configured to compress the tube against the race at one or more points along the path, the roller assembly including at least one roller;
    a drive assembly to drive the roller assembly relative to the tube along the path so as to move the liquid through the tube; and
    a coil spring operably connected to the at least one roller to adjustably bias the at least one roller against the tube, wherein the coil spring is formed of a nitinol shape memory alloy.

14. An implantable drug infusion device comprising, in combination:
    a bulkhead having a race;
    a pump tube having an inlet and an outlet and being positioned within the race;
    a roller assembly configured to compress the tube against the race at at least one point along the path, the roller assembly including at least one roller; and
    a drive assembly to drive the roller assembly relative to the tube along the path so as to move a liquid through the tube;

wherein the roller assembly comprises at least one trailing arm pivotally connected to the roller assembly, each trailing arm having a roller pivotally secured at one end of the trailing arm, a biasing member to adjustably bias the roller against the pump tube, and a tube guide extending from the other end of the trailing arm to align the pump tube with respect to a corresponding roller.

15. The implantable drug infusion device of claim 14, wherein the biasing member comprises a coil spring.

16. The implantable drug infusion device of claim 14, further comprising a support plate to secure the roller assembly and drive assembly to the bulkhead.

17. The implantable drug infusion device of claim 14, further comprising a motor assembly, the drive assembly driven by the motor assembly.

18. The implantable drug infusion device of claim 14, wherein each tube guide comprises an upper blade and a lower blade.

19. An implantable drug infusion device comprising, in combination:
    a bulkhead having a race;
    a pump tube having an inlet and an outlet and being positioned within the race;
    a roller assembly configured to compress the tube against the race at at least one point along the path, the roller assembly including at least one roller;
    a drive assembly to drive the roller assembly relative to the tube along the path so as to move a liquid through the tube; and
    a coil spring operably connected to the at least one roller to adjustably bias the at least one roller against the tube, wherein the coil spring is formed of a nitinol shape memory alloy.

20. An implantable drug infusion device comprising, in combination:
    a bulkhead having a race, a first chamber, and a second chamber;
    a pump tube having an inlet and an outlet and being positioned within the race;
    a motor assembly positioned within the first chamber; and
    a pumphead assembly positioned within the second chamber, the motor assembly driving the pumphead assembly, the pumphead assembly comprising
        a roller assembly having a hub and three trailing arms, each trailing arm being pivotally connected to the hub, having a roller pivotally secured at one end of the trailing arm, a spring to bias a corresponding roller against the pump tube, and a tube guide extending from the other end of the trailing arm to align the pump tube with respect to a corresponding roller; and
        a drive assembly to drive the roller assembly relative to the pump tube along the path so the rollers compress the pump tube to move a liquid through the pump tube.

21. The implantable drug infusion device of claim 20, wherein the pumphead assembly further comprises a support plate secured to the bulkhead.

22. The implantable drug infusion device of claim 20, wherein the race includes an inlet ramp and an outlet ramp, the inlet ramp and outlet ramp each having an arcuate geometry.

23. The implantable drug infusion device of claim 20, further comprising three hooks formed on the hub, and a pivot pin on each trailing arm, wherein the pivot pin of each trailing arm is captured by a corresponding hook on the hub.

24. The implantable drug infusion device of claim 20, wherein each tube guide comprises an upper blade and a lower blade.

* * * * *